(12) United States Patent
Flanagan (10) Patent No.: US 12,061,149 B2
(45) Date of Patent: Aug. 13, 2024

(54) SWEPT FREQUENCY FLUOROMETER

(71) Applicant: YSI, INC., Yellow Springs, OH (US)

(72) Inventor: Kevin Flanagan, Yellow Springs, OH (US)

(73) Assignee: YSI, INC., Yellow Springs, OH (US)

( * ) Notice: Subject to any disclaimer, the term of this patent is extended or adjusted under 35 U.S.C. 154(b) by 0 days.

(21) Appl. No.: 17/324,423

(22) Filed: May 19, 2021

(65) Prior Publication Data

US 2021/0364433 A1    Nov. 25, 2021

Related U.S. Application Data

(60) Provisional application No. 63/027,587, filed on May 20, 2020, provisional application No. 63/028,013, (Continued)

(51) Int. Cl.
*G01N 21/64* (2006.01)
*G01N 21/47* (2006.01)
(Continued)

(52) U.S. Cl.
CPC ..... *G01N 21/6456* (2013.01); *G01N 21/4785* (2013.01); *G01N 21/532* (2013.01);
(Continued)

(58) Field of Classification Search
CPC .............. G01N 21/6408; G01N 2201/12761
See application file for complete search history.

(56) References Cited

U.S. PATENT DOCUMENTS 2,554,321 A   5/1951 Bray
3,967,113 A   6/1976 Soodak et al.
(Continued)

FOREIGN PATENT DOCUMENTS

CN   105318898 A    2/2016
EP   3 413 035 A1   12/2018
(Continued)

OTHER PUBLICATIONS

Ming Zhao et al. "FPGA-based multi-channel fluorescence lifetime analysis of Fourier multiplexed frequency-sweeping lifetime imaging" Optical Society of America vol. 22 No. 19 (2014) (Year: 2014).*

(Continued)

*Primary Examiner* — Edwin C Gunberg
(74) *Attorney, Agent, or Firm* — Ware, Fressola, Maguire & Barber LLP

(57) ABSTRACT

A swept frequency fluorometer having a signal processor or processing module configured to:

receive signaling containing information about reflected light off one or more fluorescence species-of-interest in a liquid sample that is swept with light having a variable frequency range, the information including a characteristic optical frequency corresponding to a fluorescence species-of-interest in the liquid, and a characteristic/lifetime optical frequency corresponding to a distinct fluorescence lifetime in which the fluorescence species-of-interest remains in an excited state; and provide corresponding signaling containing information about an identity of the fluorescence species-of-interest detected and distinguished from overlapping fluorescence species in the liquid using the characteristic/lifetime optical frequency, based upon the signaling received.

14 Claims, 5 Drawing Sheets

Related U.S. Application Data filed on May 21, 2020, provisional application No. 63/028,723, filed on May 22, 2020.

(51) Int. Cl.

| | | |
|---|---|---|
| *G01N 21/53* | (2006.01) | |
| *G01N 21/82* | (2006.01) | |
| *G01N 33/08* | (2006.01) | |
| *G01N 33/18* | (2006.01) | |
| *H04N 25/46* | (2023.01) | |

(52) U.S. Cl.
CPC ............ *G01N 21/64* (2013.01); *G01N 21/82* (2013.01); *G01N 33/08* (2013.01); *G01N 33/18* (2013.01); *H04N 25/46* (2023.01); *G01N 2021/6473* (2013.01); *G01N 2021/6491* (2013.01); *G01N 2201/061* (2013.01); *G01N 2201/0633* (2013.01); *G01N 2201/0636* (2013.01); *G01N 2201/126* (2013.01); *G01N 2201/12761* (2013.01); *G01N 2201/12792* (2013.01)

(56) References Cited

U.S. PATENT DOCUMENTS

| | | | |
|---|---|---|---|
| 4,058,732 A | 11/1977 | Wieder | |
| 4,084,905 A | 4/1978 | Schreiber et al. | |
| 4,178,512 A | 12/1979 | Frungel et al. | |
| 4,937,457 A | 6/1990 | Mitchell | |
| 4,942,303 A | 7/1990 | Kolber et al. | |
| 5,257,202 A | 10/1993 | Feddersen et al. | |
| 5,294,799 A | 3/1994 | Aslund et al. | |
| 5,426,306 A | 6/1995 | Kolber et al. | |
| 5,818,582 A | 10/1998 | Fernandez et al. | |
| 5,981,957 A | 11/1999 | Cruce et al. | |
| 5,994,707 A | 11/1999 | Mendoza et al. | |
| 6,323,495 B1 | 11/2001 | Riedel | |
| 6,426,505 B1 | 7/2002 | Rao et al. | |
| 6,447,724 B1 | 9/2002 | Jensen et al. | |
| 7,582,882 B2 | 9/2009 | McLoskey et al. | |
| 9,005,988 B2 | 4/2015 | Perfect et al. | |
| 9,222,888 B2 | 12/2015 | Greenbaum et al. | |
| 9,606,059 B2 | 3/2017 | Mattos et al. | |
| 9,857,305 B2 | 1/2018 | Tokhtuev et al. | |
| 2002/0158212 A1* | 10/2002 | French ................ | B01L 3/50853 252/301.16 |
| 2003/0062485 A1 | 4/2003 | Fernandez et al. | |
| 2003/0129770 A1 | 7/2003 | Fernandez | |
| 2006/0257958 A1 | 11/2006 | Bruno | |
| 2007/0037187 A1* | 2/2007 | Alexandre ........... | C12Q 1/6837 435/6.15 |
| 2008/0204760 A1* | 8/2008 | Gollier ............... | G01N 21/7703 356/484 |
| 2009/0046295 A1 | 2/2009 | Kemp et al. | |
| 2010/0227348 A1 | 9/2010 | Petrich et al. | |
| 2016/0166144 A1 | 6/2016 | Izatt et al. | |
| 2016/0270666 A1 | 9/2016 | Vermeulen | |
| 2019/0234863 A1 | 8/2019 | Diebold et al. | |

FOREIGN PATENT DOCUMENTS

| | | |
|---|---|---|
| FR | 2817346 B1 | 11/2008 |
| JP | 5898077 B2 | 4/2016 |
| JP | 6314872 B2 | 4/2018 |
| WO | 2000/009753 A1 | 2/2000 |
| WO | 2015/080549 A1 | 6/2015 |
| WO | 2016/028996 A1 | 2/2016 |

OTHER PUBLICATIONS

Benjamin D. Venetta, "Microscope Phase Fluorometer for Determining the Fluorescence Lifetimes of Fluorochromes" Rev. Sci. Instrum. 30, 450-457 (1959) (Year: 1959).*
Hironobu Shibata and Tetsuo Iwata, "Construction of a Fourier-transform phase-modulation fluorometer" Proc. SPIE 6204 (2005) (Year: 2005).*
Iwata et al. "Analysis of Data Obtained from a Frequency-Multiplexed Phase-Modulation Fluorometer Using an Autoregressive Model" Applied Spectroscopy, vol. 61, No. 9 (2007) (Year: 2007).*
English Abstract of CN105318898A.
English Translation of JP5898077B2.
McDonagh, C., et al. "Phase fluorometric dissolved oxygen sensor." Sensors and Actuators B: Chemical 74.1-3 (2001): https://www.researchgate.net/profile/Riaz_Khan14/post/ls_there_an_easy_way_to_measure_the_amount_of_oxygen_in_a_gel/attachment/59d6352879197b8077992c34/AS:383267204288512@1468389430112/download/phase_fluorome tric_dissolved_oxygen_sensor.pdf; pp. 124-130; Section "3.1. Principles of phase fluorometry" on p. 125.
Leeuw, Thomas, Emmanuel Boss, and Dana Wright. "In situ measurements of phytoplankton fluorescence using low cost electronics." Sensors 13.6 (2013); https://www .mdpi.com/1424-8220/13/6/7872/pdf; pp. 7872-7883; Section 3.4 "Improvements" on p. 7880.
Gratton, Enrico, David M. Jameson, and Robert D. Hall. "Multifrequency phase and modulation fluorometry." Annual review of biophysics and bioengineering 13.1 (1984); https://cloudfront.escho larship.org/dist/prd/content/qt7b52q41w/qt7b52q41w.pdf; pp. 105-124.
Alcala, J. Ricardo, Enrico Gratton, and David M. Jameson. "A multifrequency phase fluorometer using the harmonic content of a mode-locked laser." (1985); https://clo udfront.escholarship.org/dist/prd/content/qt3mf1q4fd/qt3mf1q4fd.pdf; pp. 225-250.
English translation of JP 6314872B2.
English translation of FR 2817346B2.

* cited by examiner

*FIG. 1*

Overlapping Fluorophores with distinct (FLT)

Apparatus, including a swept frequency fluorometer, 10

A light source 20 configured to provide light on a liquid sample having one or more fluorescence species-of-interest, the light having a variable frequency range with an initial frequency $f_i$ and a final frequency $f_f$.

A light sensor, 30 configured to sense reflected light off the fluorescence species-of-interest in the liquid sample and provide signaling containing information about the reflected light off the one or more fluorescemce species-of-interest in the liquid sample that is swept with the light having the variable frequency range, the information including a characteristic optical frequency corresponding to a fluorescence species- of-interest in the liquid, and a characteristic/lifetime optical frequency corresponding to a distinct fluorescence lifetime in which the fluorescence species-of-interest remains in an excited state.

Signal processor, 40 configured at least to: receive signaling; and provide corresponding signaling containing information about an identity of the fluorescence species-of-interest detected and distinguished from overlapping fluorescence species in the liquid using the characteristics/lifetime optical frequency, based upon the signaling received.

Other signal processor circuits, circuitry, or components, 50 that do not form part of the underlying invention, e.g., including input/output modules/modems, one or more memory modules (e.g., RAM, ROM, etc.), data, address and control busing architecture, etc.

*FIG. 4*: Swept frequency fluorometer, 10

| (r1, c1) | (r1, c2) | (r1, c3) | (r1, c4) | (r1, c5) | (r1, c6) | (r1, c7) | (r1, c8) | ... | (r1, cn) |
| (r2, c1) | (r2, c2) | (r2, c3) | (r2, c4) | (r2, c5) | (r2, c6) | (r2, c7) | (r2, c8) | ... | (r2, cn) |
| (r3, c1) | (r3, c2) | (r3, c3) | (r3, c4) | (r3, c5) | (r3, c6) | (r3, c7) | (r3, c8) | ... | (r3, cn) |
| | | | | | ... | | | | |
| (rn, c1) | (rn, c2) | (rn, c3) | (rn, c4) | (rn, c5) | (rn, c6) | (rn, c7) | (rn, c8) | ... | (rn, cn) |

*FIG. 5*: Linear sensor array

SWEPT FREQUENCY FLUOROMETER

CROSS-REFERENCE TO RELATED APPLICATIONS

This application claims benefit to provisional patent application Ser. Nos. 63/027,587, filed 20 May 2020; 63/028,013, filed 21 May 2020, and 63/028,723, filed 22 May 2020, which are all incorporated by reference in its entirety.

BACKGROUND OF THE INVENTION

1. Field of Invention

This invention relates to a fluorometer for identifying species in a liquid, including where the liquid contains overlapping species.

2. Description of Related Art

In general, traditional fluorescence sensing techniques suffer from spectrally broad features often yielding ambiguous identification of the water species, especially when the fluorescence signatures of multiple species overlap.

In particular, traditional (single channel) fluorometers typically consist of a single excitation light source (at specified optical wavelength) used to optically excite the water parameter of interest and re-emit optical light (at a longer optical wavelength) specific to the water parameter of interest. Such sensors often utilize lock-in detection which selectively measures sinusoidal signals at a fixed (in-band) frequency, and reject signals that possess other frequencies (out-of-band frequencies).

There is a need in the art for a better fluorometer, e.g., for identifying species in a liquid that contains overlapping species.

SUMMARY OF THE INVENTION

In summary, the sensor according to the present invention differs from traditional fluorometers in that the lock-in frequency for this sensor is to be "swept", i.e., gradually increased from some initial modulation frequency, $f_i$, to some final modulation frequency, $f_f$. Every fluorescence species possesses its own distinct fluorescence "lifetime" (FLT) in which an excited fluorophore (excited by the excitation optical wavelength) remains in an excited state for a finite amount of time e.g., the lifetime [sec.], before returning to the ground state accompanied by subsequent emission. As the signal's modulation frequency is swept through the characteristic frequency of the species, $f=(1/\text{lifetime})$ [Hz], the phase of the signal undergoes an overall relative phase shift of 90 degrees in addition to a decrease in signal amplitude. The midpoint of the relative phase transition (45 degrees) precisely corresponds to the characteristic/lifetime frequency of the fluorescence species. In short, if there is uncertainty in the identity of overlapping fluorescence species, then knowledge of the lifetime can further delineate between the two species.

In effect, fluorescence lifetime (through swept excitation frequency) promises another dimension of information, adding depth to the "fingerprint" of the water body.

The fluorometer according to the present invention will measure: Ex/Em+Fluorescence lifetime for providing an enhanced detection technique.

Moreover, one key to this invention pertains specifically to the opto-mechanical configuration which utilizes a wide linear array along the length of the quasi-collimated light.

The design herein is compatible with non-intensity-based determinations of turbidity.

By way of example, the present invention has applications in environmental water quality monitoring

Specific Embodiments

By way of example, and according to some embodiments, the present invention may include, or take the form of, apparatus featuring a signal processor or processing module configured to:

receive signaling containing information about reflected light off one or more fluorescence species-of-interest in a liquid sample that is swept with light having a variable frequency range, the information including a characteristic optical frequency corresponding to a fluorescence species-of-interest in the liquid, and a characteristic/lifetime optical frequency corresponding to a distinct fluorescence lifetime in which the fluorescence species-of-interest remains in an excited state; and provide corresponding signaling containing information about an identity of the fluorescence species-of-interest detected and distinguished from overlapping fluorescence species in the liquid using the characteristic/lifetime optical frequency, based upon the signaling received.

The apparatus may include one or more of the following additional features:

The apparatus may include a light sensor configured to sense the light across the variable frequency range, and provide the signaling received by the signal processor or processing module.

The light sensor may be a linear sensor array configured to sense the light across the variable frequency range along the length of a light source providing the light.

The apparatus may include a light source configured to sweep excitation light having an excitation optical wavelength across the variable frequency range to excite the one or more fluorescence species-of-interest.

The light source may be a swept-frequency light source, including a quasi-collimated light source.

The variable frequency range may include a lock-in frequency that is swept by gradually increasing the excitation light from an initial modulation frequency $f_i$ to a final modulation frequency $f_f$.

The variable frequency range may include a mid-point frequency that corresponds to the characteristic/lifetime optical frequency.

The apparatus may include, or take the form of, a swept frequency fluorometer.

A Swept Frequency Fluorometer

By way of further example, and according to some embodiments, the present invention may take the form of a swept frequency fluorometer featuring a light source, a light sensor and a signal processor or processing module.

The light source may be configured to provide excitation light on a liquid sample having one or more fluorescence species-of-interest, the excitation light having a variable frequency range with an initial frequency $f_i$ and a final frequency of $f_f$.

The light sensor may be configured to sense reflected light off the one or more fluorescence species-of-interest in the liquid sample and provide signaling containing information about the reflected light off the one or more fluorescence species-of-interest in the liquid sample that is swept with the excitation light having the variable frequency range, the information including a characteristic optical frequency corresponding to a fluorescence species-of-interest in the liquid, and a characteristic/lifetime optical frequency corresponding to a distinct fluorescence lifetime in which the fluorescence species-of-interest remains in an excited state.

The signal processor or processing module may be configured to:
receive the signaling, and
provide corresponding signaling containing information about an identity of the fluorescence species-of-interest detected and distinguished from overlapping fluorescence species in the liquid using the characteristic/lifetime optical frequency, based upon the signaling received The swept frequency fluorometer may also include one or more of the features set forth above.

The Method

By way of still further example, and according to some embodiments, the present invention may include a method featuring:
receiving, with a signal processor or processing module, signaling containing information about reflected light off one or more fluorescence species-of-interest in a liquid sample that is swept with light having a variable frequency range, the information including a characteristic optical frequency corresponding to a fluorescence species-of-interest in the liquid, and a characteristic/lifetime optical frequency corresponding to a distinct fluorescence lifetime in which the fluorescence species-of-interest remains in an excited state; and
providing, with the signal processor or processing module, corresponding signaling containing information about an identity of the fluorescence species-of-interest detected and distinguished from overlapping fluorescence species in the liquid using the characteristic/lifetime optical frequency, based upon the signaling received.

The method may also include one or more of the features set forth above.

Computer-Readable Storage Medium

By way of still further example, and according to some embodiments of the present invention, the present invention may also take the form of a computer-readable storage medium having computer-executable components for performing the steps of the aforementioned method. The computer-readable storage medium may also include one or more of the features set forth above.

BRIEF DESCRIPTION OF THE DRAWING

The drawing, which are not necessarily drawn to scale, includes FIGS. 1-5, as follows:

FIG. 2 includes FIGS. 2A and 2B and is an Excitation Emission Matrix (EEM) plot of two overlapping species (TrisBipy Ru (II) and Pt Porphyrin). For clarity, the plots are stacked (not overlaid). The axes and scale are the same in both frames.

FIG. 4 is a block diagram of a swept frequency fluorometer, e.g., having a light source, a light sensor and a signal processor or processing module for performing signal processing functionality, according to some embodiments of the present invention.

To reduce clutter in the drawing, each Figure in the drawing does not necessarily include every reference label for every element shown therein.

DETAILED DESCRIPTION OF BEST MODE OF THE INVENTION

FIG. 4 shows apparatus 10, including a swept frequency fluorometer, according to the present invention, e.g., having a light source 20 such as quasi-collimated light source, a light sensor 30 such as a linear sensor array, and a signal processor or processing module 40.

The light source 20 may be configured to provide light on a liquid sample having one or more fluorescence species-of-interest, the light having a variable frequency range with an initial frequency $f_i$ and a final frequency $f_f$. According to some embodiments, the light source 20 may be configured to respond to a light source control signal, e.g., provided by the signal processor or processing module 40 and provide the light having the variable frequency range.

The light sensor 30 may be configured to sense reflected light off the fluorescence species-of-interest in the liquid sample and provide signaling containing information about the reflected light off the one or more fluorescence species-of-interest in the liquid sample that is swept with the light having the variable frequency range, the information including a characteristic optical frequency corresponding to a fluorescence species-of-interest in the liquid, and a characteristic/lifetime optical frequency corresponding to a distinct fluorescence lifetime in which the fluorescence species-of-interest remains in an excited state. According to some embodiments, the light sensor 30 may be configured to respond to a light sensor control signal, e.g., provided by the signal processor or processing module 40 and sense the reflected light.

The signal processor or processing module 40 may be configured to
receive the signaling; and
provide corresponding signaling containing information about an identity of the fluorescence species-of-interest detected and distinguished from overlapping fluorescence species in the liquid using the characteristic/lifetime optical frequency, based upon the signaling received.

According to some embodiments, the signal processor or processing module 40 may be configured to provide the light source control signal and/or the light sensor control signal, e.g., to the light source 20 and/or light sensor 30.

The Light Source 20

Figure 1:
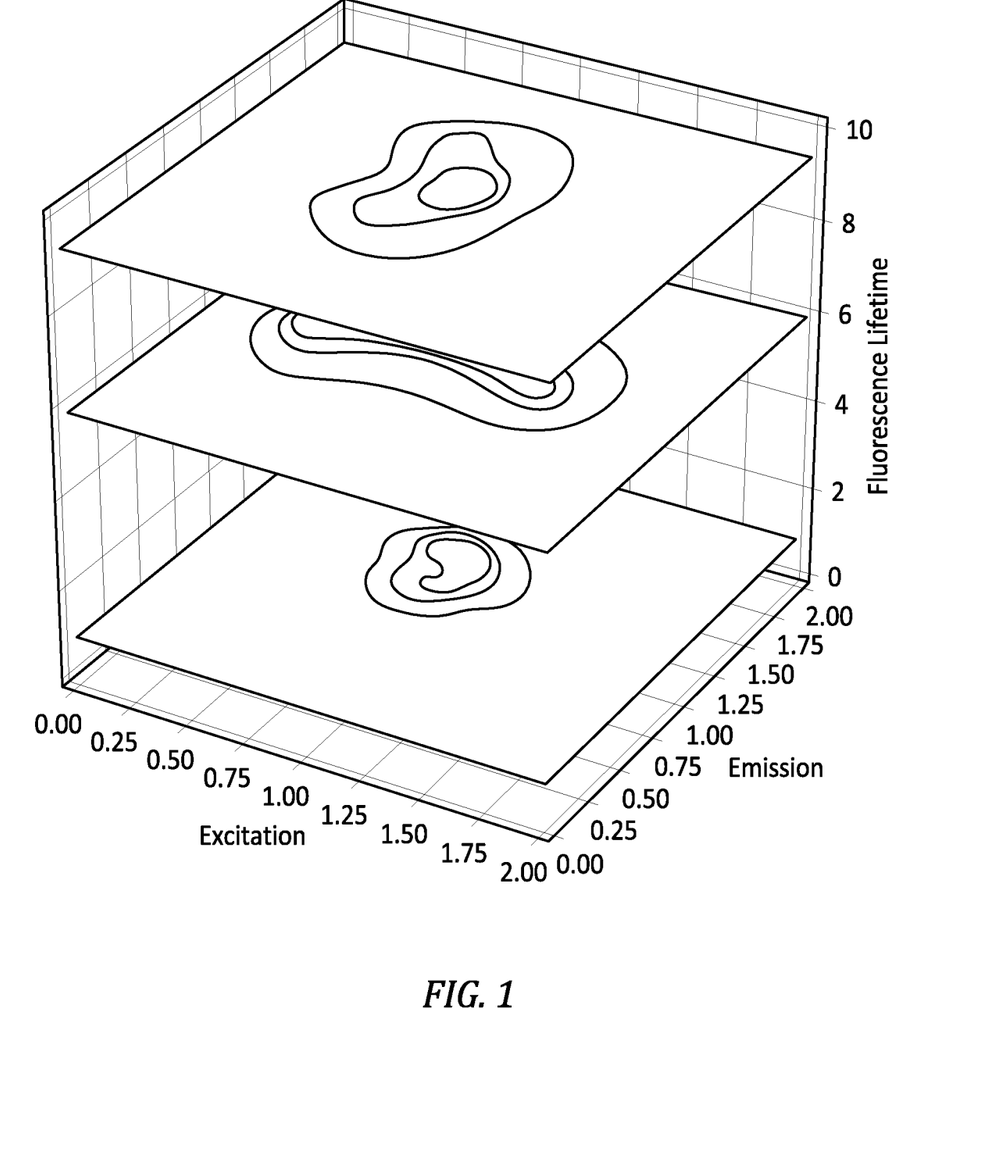
FIG. 1 is a graph of excitation, emission and fluorescence lifetime, and provides a concept plot of the fluorometer according to the present invention, in which three different, but overlapping species can be measured within the same Ex/Em band pass region. Traditional fluorometers do not have the ability to distinguish between the three species, but with the rendering of fluorescence lifetime, a distinction can be made according to the present invention.
Figure 2A:
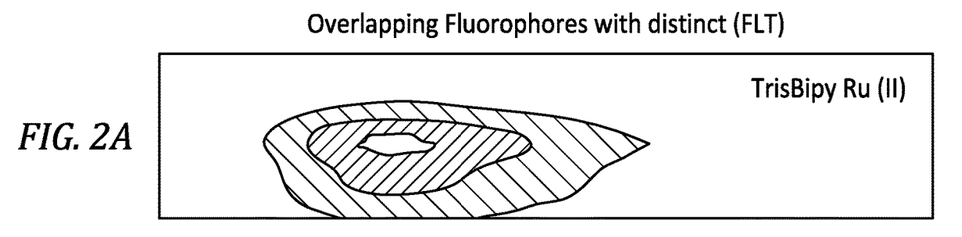
Figure 2B:
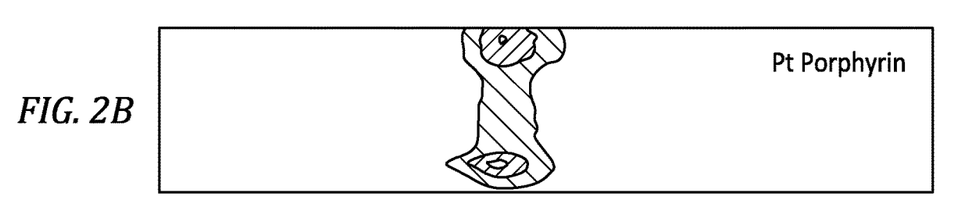
Figure 3:
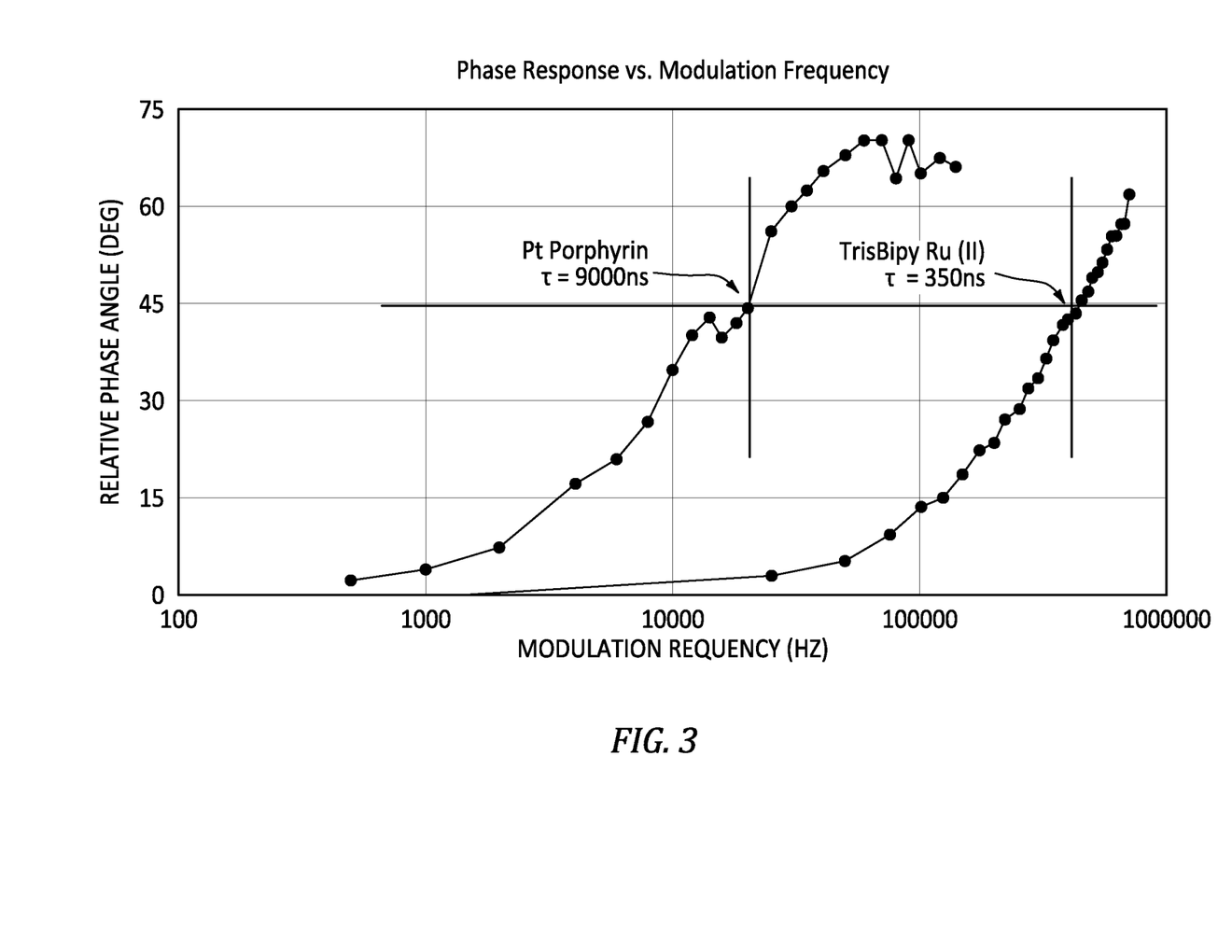
FIG. 3 is a graph or plot of relative phase angle (Deg.) vs. swept modulation excitation frequency (Hz) of the respective species (TrisBipy Ru (II) and Pt Porphyrin), e.g., showing how the phase responses are completely distinguishable though their respective EEM signatures occupy the same region of the EEM chart, causing ambiguity.
Figure 5:
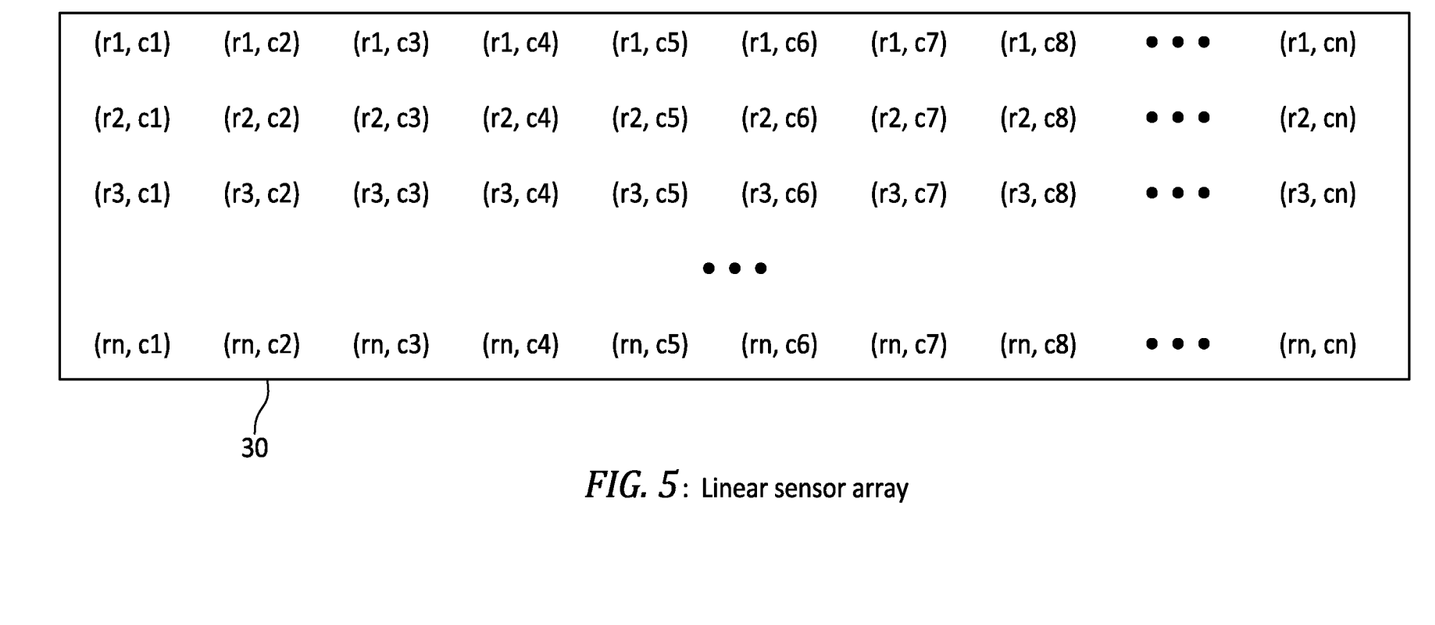
FIG. 5 is a diagram of the light sensor in the form of a linear sensor array, e.g., having rows and columns of optical elements, according to some embodiments of the present invention.

By way of example, the light source 20 may be configured to provide the light, including quasi-collimated light, along a corresponding length of the linear sensor array 30, e.g., as shown in FIG. 5, through a liquid sample arranged in relation to the light source 20 and the linear sensor array 30 so as to reflect the light off the one or more fluorescence species-of-interest in the liquid sample being monitored or tested onto the linear sensor array 30.

As a person skilled in the art would appreciate, quasi-collimated light sources are known in the art, and the scope of the invention is not intended to be limited to any particular type or kind thereof either now known or later developed in the future.

The Linear Sensor Array 30

By way of example, the linear sensor array 30 may include, e.g., a linear photodiode array, a linear charge-coupled device (CCD) array, or a linear CMOS array. In particular, the linear sensor array 30 may include a two-dimensional array of rows and columns of optical elements (r1, c1; r1, c2; r1, c3; r1, c4; r1, c5; r1, c6; r1, c7; r1, c8; . . . ; r1, cn; r2, c1; r2, c2; r2, c3; r2, c4; r2, c5; r2, c6; r2, c7; r2, c8; . . . ; r2, cn; r3, c1; r3, c2; r3, c3; r3, c4; r3, c5; r3, c6; r3, c7; r3, c8; . . . ; r3, cn; . . . ; rn, c1; rn, c2; rn, c3; rn, c4; rn, c5; rn, c6; rn, c7; rn, c8; . . . ; rn, cn) like that shown in FIG. 5, e.g., that are individually addressable. Linear sensor arrays are known in the art, and the scope of the invention is not intended to be limited to any particular type or kind thereof either now known or later developed in the future.

By way of example, linear sensors arrays are disclosed in the following U.S. Pat. Nos. 9,020,202; 8,022,349; 7,956,341; 7,040,538; 5,252,818; and 4,193,057, which are all hereby incorporated by reference.

The Signal Processor or Processing Module 40

By way of example, the signal processor or processing module 40 may be configured to determine the one or more fluorescence species-of-interest based upon the frequencies so determined, and then determine the concentration of turbidity of the liquid, based upon the same. Techniques for processing signaling containing information about sensed optical frequencies, e.g., in relation to the concentration of turbidity in the liquid, are known in the art, and the scope of the invention is not intended to be limited to any particular type or kind thereof either now known or later developed in the future.

Implementation of Signal Processing Functionality

By way of example, the functionality of the signal processor or processing module 40 may be implemented using hardware, software, firmware, or a combination thereof. In a typical software implementation, the signal processor 40 would include one or more microprocessor-based architectures having, e. g., at least one signal processor or microprocessor. One skilled in the art would be able to program with suitable program code such a microcontroller-based, or microprocessor-based, implementation to perform the signal processing functionality disclosed herein without undue experimentation.

The scope of the invention is not intended to be limited to any particular implementation using technology either now known or later developed in the future. The scope of the invention is intended to include implementing the functionality of the signal processor(s) as stand-alone processor, signal processor, or signal processor module, as well as separate processor or processor modules, as well as some combination thereof.

By way of example, the apparatus 10 may also include, e.g., other signal processor circuits or components generally indicated 50, including random access memory or memory module (RAM) and/or read only memory (ROM), input/output devices and control, and data and address buses connecting the same, and/or at least one input processor and at least one output processor, e.g., which would be appreciate by one skilled in the art.

By way of further example, the signal processor may include, or take the form of, some combination of a signal processor and at least one memory including a computer program code, where the signal processor and at least one memory are configured to cause the system to implement the functionality of the present invention, e.g., to respond to signaling received and to determine the corresponding signaling, based upon the signaling received.

The Scope of the Invention

While the invention has been described with reference to an exemplary embodiment, it will be understood by those skilled in the art that various changes may be made, and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. A fluorometer for monitoring environmental water quality by identifying a fluorescence species-of-interest in a water sample that contains overlapping fluorescence species, comprising:

a signal processor or processing module configured to:
receive signaling containing information about excitation light reflected off one or more fluorescence species-of-interest in a water sample, the excitation light having a modulation frequency and being swept across a variable frequency range from an initial modulation frequency $f_i$ to a final modulation frequency $f_f$, the information including a characteristic optical frequency corresponding to a fluorescence species-of-interest in the water sample, and a characteristic/lifetime optical frequency corresponding to a distinct fluorescence lifetime in which the fluorescence species-of-interest remains in an excited state, the modulation frequency being swept across the variable frequency range including the characteristic optical frequency corresponding to the fluorescence species-of-interest in the water sample, and also including a midpoint of a relative phase transition at 45 degrees corresponding to the characteristic/lifetime optical frequency of the fluorescence species-of-interest; and provide corresponding signaling containing information about an identity of the fluorescence species-of-interest detected and distinguished from overlapping fluorescence species in the water sample using the characteristic/lifetime optical frequency, based upon the signaling received.

2. A fluorometer according to claim 1, wherein the apparatus comprises a light sensor configured to sense the excitation light across the variable frequency range, and provide the signaling.

3. A fluorometer according to claim 2, wherein the light sensor is a linear sensor array configured to sense the excitation light across the variable frequency range along the length of a light source providing the excitation light.

4. A fluorometer according to claim 1, wherein the apparatus comprises a light source configured to sweep the excitation light across the variable frequency range to excite the one or more fluorescence species-of-interest.

5. A fluorometer according to claim 4, wherein the light source is a swept-frequency light source, including a quasi-collimated light source.

6. A fluorometer according to claim 1, wherein the apparatus is a swept frequency fluorometer.

7. A method for monitoring environmental water quality by identifying a fluorescence species-of-interest in a water sample that contains overlapping fluorescence species, comprising:
    receiving, with a signal processor or processing module forming part of a fluorometer, signaling containing information about excitation light reflected off one or more fluorescence species-of-interest in a water sample, the excitation light having a modulation frequency and being swept across a variable frequency range from an initial modulation frequency $f_i$ to a final modulation frequency $f_f$, the information including a characteristic optical frequency corresponding to a fluorescence species-of-interest in the water sample, and a characteristic/lifetime optical frequency corresponding to a distinct fluorescence lifetime in which the fluorescence species-of-interest remains in an excited state, the modulation frequency being swept across the variable frequency range including the characteristic optical frequency corresponding to the fluorescence species-of-interest in the water sample, and also including a midpoint of a relative phase transition at 45 degrees corresponding to the characteristic/lifetime optical frequency of the fluorescence species-of-interest; and
    providing, with the signal processor or processing module, corresponding signaling containing information about an identity of the fluorescence species-of-interest detected and distinguished from overlapping fluorescence species in the water sample using the characteristic/lifetime optical frequency, based upon the signaling received.

8. A method according to claim 7, wherein the method comprises configuring a light sensor to sense the excitation light across the variable frequency range, and provide the signaling.

9. A method according to claim 8, wherein the method comprises configuring the light sensor as a linear sensor array to sense the excitation light across the variable frequency range along the length of a light source providing the excitation light.

10. A method according to claim 7, wherein the method comprises configuring a light source to sweep the excitation light across the variable frequency range to excite the one or more fluorescence species-of-interest.

11. A method according to claim 10, wherein the method comprises configuring the light source as a swept-frequency light source, including a quasi-collimated light source.

12. A method according to claim 7, wherein the method comprises configuring the signal processor or signal processing module as part of a swept frequency fluorometer.

13. A swept frequency fluorometer for monitoring environmental water quality by identifying a fluorescence species-of-interest in a water sample that contains overlapping fluorescence species, comprising:
    a light source configured to provide excitation light on a water sample having one or more fluorescence species-of-interest, the excitation light having a modulation frequency and being swept across a variable frequency range from an initial frequency $f_i$ to a final frequency of $f_f$, the modulation frequency being swept across the variable frequency range including the characteristic optical frequency corresponding to the fluorescence species-of-interest in the water sample, and also including a midpoint of a relative phase transition at 45 degrees corresponding to the characteristic/lifetime optical frequency of the fluorescence species-of-interest;
    a light sensor configured to sense the excitation light reflected off the fluorescence species-of-interest in the water sample and provide signaling containing information about the excitation light reflected off the one or more fluorescence species-of-interest in the water sample, the information including a characteristic optical frequency corresponding to a fluorescence species-of-interest in the water sample, and a characteristic/lifetime optical frequency corresponding to a distinct fluorescence lifetime in which the fluorescence species-of-interest remains in an excited state; and
    a signal processor or processing module configured to:
        receive the signaling, and
        provide corresponding signaling containing information about an identity of the fluorescence species-of-interest detected and distinguished from overlapping fluorescence species in the water sample using the characteristic/lifetime optical frequency, based upon the signaling received.

14. A swept frequency fluorometer according to claim 13, wherein
    the light source is a swept-frequency light source, including a quasi-collimated light source; and
    the light sensor is a linear sensor array configured to sense the excitation light across the variable frequency range along the length of a light source providing the excitation light.

* * * * *